(12) United States Patent
Muller et al.

(10) Patent No.: US 11,832,937 B2
(45) Date of Patent: Dec. 5, 2023

(54) INJECTOR FOR TRANSCUTANEOUSLY INTRODUCING A SENSOR INTO A PATIENT

(71) Applicant: EyeSense GmbH, Grossostheim (DE)

(72) Inventors: Achim Muller, Grossostheim (DE); Tom Meissner-Braun, Uberlingen (DE); Matthias Pischan, Darmstadt (DE)

(73) Assignee: EYESENSE GMBH, Großostheim (DE)

( * ) Notice: Subject to any disclaimer, the term of this patent is extended or adjusted under 35 U.S.C. 154(b) by 808 days.

(21) Appl. No.: 16/253,638

(22) Filed: Jan. 22, 2019

(65) Prior Publication Data

US 2019/0223767 A1 Jul. 25, 2019

(30) Foreign Application Priority Data

Jan. 22, 2018 (DE) .......................... 102018101275.6

(51) Int. Cl.
*A61B 5/145* (2006.01)
*A61B 17/34* (2006.01)
(Continued)

(52) U.S. Cl.
CPC ........ *A61B 5/14503* (2013.01); *A61B 5/0031* (2013.01); *A61B 5/14532* (2013.01);
(Continued)

(58) Field of Classification Search
CPC .......... A61B 5/14532; A61B 2560/063; A61B 5/14503; A61B 5/6849; A61B 2017/3407; A61B 2017/347

See application file for complete search history.

(56) References Cited

U.S. PATENT DOCUMENTS

| 5,390,671 A | 2/1995 | Lord et al. |
| 9,931,066 B2 | 4/2018 | Pace et al. |

(Continued)

FOREIGN PATENT DOCUMENTS

| CN | 103476453 | 12/2013 |
| EP | 2250959 | 11/2010 |

(Continued)

*Primary Examiner* — Carrie R Dorna
*Assistant Examiner* — Karen E Toth
(74) *Attorney, Agent, or Firm* — Volpe Koenig (57) ABSTRACT

An injector for transcutaneously introducing a sensor into a patient, including a cannula, a sensor arranged in the cannula, a base element, a sliding element arranged displaceably on the base element in an injection direction, for transcutaneously introducing the cannula having the sensor into the patient in an injection operation. The cannula has a slot in a longitudinal direction of the cannula. The injector has a holding element arranged displaceably on the base element that, in an ejection operation, prevents the sensor from being pulled out as the cannula is withdrawn, by engaging in a distal end region of the sensor through the slot into the cannula. The holding element and/or base element have at least one fixing arrangement to automatically lock the holding element on the base element when the cannula is introduced transcutaneously into the patient. A method for transcutaneously introducing a sensor into a patient is also provided.

16 Claims, 12 Drawing Sheets

(51) Int. Cl.
  *A61B 5/00* (2006.01)
  *A61B 90/00* (2016.01)

(52) U.S. Cl.
  CPC ...... *A61B 17/3421* (2013.01); *A61B 17/3468* (2013.01); *A61B 5/14507* (2013.01); *A61B 5/14546* (2013.01); *A61B 5/683* (2013.01); *A61B 2090/034* (2016.02); *A61B 2090/0811* (2016.02); *A61B 2560/063* (2013.01); *A61M 2205/3507* (2013.01); *A61M 2230/201* (2013.01)

(56) References Cited

U.S. PATENT DOCUMENTS

| | | |
|---|---|---|
| 10,898,644 B2 | 1/2021 | Gyrn |
| 2004/0133164 A1 | 7/2004 | Funderburk et al. |
| 2008/0249466 A1 | 10/2008 | Aubert et al. |
| 2011/0040245 A1 | 2/2011 | Andrews |
| 2011/0190603 A1 | 8/2011 | Stafford |
| 2012/0078072 A1 | 3/2012 | Roesicke et al. |
| 2012/0184835 A1 | 7/2012 | Kube et al. |
| 2015/0190076 A1* | 7/2015 | Ohkoshi ............ A61B 5/14503 600/309 |
| 2016/0008028 A9* | 1/2016 | Matsumoto ............ A61B 5/74 600/302 |
| 2016/0243302 A1 | 8/2016 | Gyrn |
| 2016/0310051 A1 | 10/2016 | Brister et al. |
| 2017/0303831 A1 | 10/2017 | Tsubouchi et al. |

FOREIGN PATENT DOCUMENTS

| | | |
|---|---|---|
| EP | 2826422 A1 | 1/2015 |
| JP | 210507456 A | 3/2010 |
| JP | 2016128031 A | 7/2016 |
| WO | 2006092317 | 9/2006 |
| WO | 2008051920 A2 | 5/2008 |
| WO | 2009103759 | 8/2009 |
| WO | 2013136968 A1 | 9/2013 |
| WO | 2016128334 | 8/2016 |

* cited by examiner

INJECTOR FOR TRANSCUTANEOUSLY INTRODUCING A SENSOR INTO A PATIENT

INCORPORATION BY REFERENCE

The following documents are incorporated herein by reference as if fully set forth: German Patent Application No. 10 2018 101 275.6, filed Jan. 22, 2018.

BACKGROUND

The invention relates to an injector for transcutaneously introducing a sensor into a patient.

The introducing of a sensor into a patient is necessary for diverse medical applications, in particular in order to obtain readings from the patient, such as, for example, glucose values or lactose values.

US 2004/0133164 A1 discloses an injector for transcutaneously introducing a sensor into a patient, in which a slotted cannula and a sensor located therein are introduced transcutaneously into a patient by means of a sliding element. For this purpose, the cannula has a slot continuously in the longitudinal direction of the cannula. When the cannula is pulled out, the sensor is held on the patient's tissue by friction, in particular by means of a barb, in order not to be pulled out.

However, more freedom in respect of the geometry of the sensor and fewer demands in respect of the frictional properties between sensor and tissue are desirable.

SUMMARY

The present invention is based on the object of providing an injector for transcutaneously introducing a sensor into a patient, said injector placing fewer demands on the retaining force of the sensor in the patient's tissue during pulling out of the cannula.

This object is achieved by an injector having one or more features of the invention. Advantageous refinements of the injector according to the invention are described below and in the claims.

The injector according to the invention for transcutaneously introducing a sensor into a patient has a cannula, a sensor arranged in the cannula, a base element, a sliding element arranged displaceably on the base element in an injection direction, for transcutaneously introducing the cannula having the sensor into the patient in an injection operation. During the injection operation, cannula and sensor are therefore introduced transcutaneously into the patient by displacement of the sliding element in an injection direction (in the direction of the patient). The cannula has a slot at least in a proximal region in a longitudinal direction of the cannula.

It is essential that the injector has a holding element which is arranged on the base element so as to be displaceable in order, in an injection operation, when pulling the cannula out of the patient, to prevent, via the holding element, the sensor from being pulled out. The holding element engages in the region of a distal end of the sensor through a slot into the cannula.

Holding element and/or base element have at least one fixing arrangement, and therefore, in the state of the cannula introduced transcutaneously into the patient, the holding element can be automatically locked indirectly or preferably directly on the base element.

In the injection operation, cannula, sensor and holding element are therefore displaced by the sliding element from a distal starting position to a proximal end position relative to the base element, and therefore during the injection operation, sensor and cannula are introduced transcutaneously in the injection direction into the patient.

Since the holding element engages in the region of a distal end of the sensor through the slot into the cannula that is designed for automatic locking indirectly or preferably directly on the base element, the locking of the holding element takes place in the end position of the injection operation, and therefore, when the cannula is pulled out counter to the injection direction in an ejection operation, the holding element does not undertake this movement and, by engaging in the slot of the cannula in the region of the distal end of the sensor, in particular above the distal end of the sensor, also prevents movement of the sensor and therefore pulling out of the sensor. The sensor therefore remains in the injection position, in particular in a transcutaneously injection position, even during the ejection operation, irrespective of a possible friction or adhesion between sensor and patient's tissue.

In an advantageous embodiment, after injection of the sensor, the injector is removed in order to connect a detection element on the patient to the sensor and to record data and preferably to wirelessly transmit same to an evaluation unit.

In an advantageous manner, holding element and sensor are therefore formed separably and therefore, when the injector is removed, the holding element can also be removed without pulling out the sensor. In particular, it is therefore advantageous to design holding element and sensor as separate units.

In an advantageous embodiment, the fixing arrangement is designed as a latching element and one of the two elements—holding element and base element—has the latching element and the other of the two elements has a corresponding depression and/or recess for the latching element. In particular, the fixing arrangement preferably has at least one latching lug which engages at the end of the injection operation into a corresponding depression and/or recess and thereby automatically locks the holding element on the base element. Similarly, the base element can conversely have the latching lug which engages at the end of the injection operation into a corresponding depression and/or recess of the holding element.

The cannula is preferably arranged at its distal end on a cannula upper part, which is arranged displaceably on the base element, and the sliding element and cannula upper part are designed so as to interact in such a manner that, during the injection operation, the cannula upper part can be displaced in an injection direction by the sliding element. In this preferred embodiment, the action of force on the cannula therefore takes place indirectly by the user displacing the sliding element in the direction of the patient and an action of force thereby taking place on the cannula via the cannula upper part in order to insert the cannula transcutaneously into the patient.

The holding element is advantageously designed here so as to interact with the cannula upper part in such a manner that, during the injection operation, the holding element is displaceable in the injection direction by the cannula upper part.

This permits a structurally simple configuration, and therefore, during the injection operation, an action of force of the sliding element takes place on the holding element via the cannula upper part. The holding element is preferably arranged on that side of the cannula upper part which faces the patient.

In particular, it is advantageous for the holding element to be designed in a manner surrounding the cannula in order to obtain a structurally simple configuration.

The cannula is preferably connected fixedly, in particular preferably non-releasably, to the upper part. The cannula upper part advantageously surrounds the cannula at a distal end of the cannula.

The cannula upper part advantageously has a central element and at least one guide extension, in particular a guide pin. The base element preferably has at least one guide wall with a slot for the guide extension of the cannula upper part, in order to guide the cannula upper part in the injection direction. In this advantageous refinement, the cannula is arranged on the central element. The sliding element advantageously engages on the guide extension, and therefore, when the sliding element is actuated, force is transmitted via the guide extension on the central element to the cannula. In particular, it is advantageous that the guide extension penetrates the guide wall of the base element and the sliding element is designed so as to engage on the guide extension on that side of the guide wall which faces away from the central element of the cannula upper part. This provides an effective guidance of the cannula upper part in the injection direction through the guide wall and the guide slot in the guide wall.

In an advantageous development, tilting of the cannula upper part during displacement in the injection direction is avoided by a respective guide extension being formed on two opposite sides on the cannula upper part and the base element correspondingly having at least two guide slots in the injection direction for the two guide extensions and the sliding element being designed so as to engage on both guide extensions.

The two guide slots can be formed here in a common guide wall of the base element. In particular, it is advantageous that the basic wall is designed in a manner surrounding the central element of the cannula upper part and preferably also the holding element. In particular, a guide wall in the form of a hollow cylinder is advantageous for a stable construction. It also lies within the scope of the invention that the base element has a plurality of guide walls for the cannula upper part and preferably for the holding element.

In an advantageous refinement, the injector has an ejection element, in particular an ejection spring, and a locking element, in particular an ejection spring holding element. The ejection spring holding element is designed so as to be fixable on the base element, and therefore the ejection spring can be fixed in a tensioned or compressed state by the ejection spring holding element.

By this, the ejection spring can be arranged, for example, in a compressed state by the manufacturer, and therefore the energy stored by this can be used for ejecting the cannula and therefore automatic ejection takes place.

The sliding element is advantageously designed here so as to interact with the locking element, and therefore the locking element can be released from a fixing position by the sliding element at the end of the injection operation, in particular preferably by rotation of the locking element by the sliding element, preferably by rotation about an injection axis.

The injection axis corresponds to the axis along which the cannula and the sensor are displaced in the injection direction during the injection operation and along which the cannula is displaced counter to the injection direction during the ejection operation. The injection axis preferably runs through a center axis of the cannula.

The sliding element and the locking element are advantageously arranged on the base element so as to be rotatable about a common injection axis. This results in a structurally simple design.

The base element and/or the sliding element advantageously have at least one bevel, in particular a slotted guide, which is arranged in such a manner that, during the injection operation, rotation of the sliding element relative to the base element takes place in a proximal end region when the sliding element is displaced in the injection direction. By this arrangement, rotation of the sliding element is obtained in a structurally simple manner when the cannula is completely or virtually completely introduced, in order to release the locking element and to initiate expansion or contraction of the ejection spring when the cannula is ejected.

The sliding element and the locking element therefore advantageously have corresponding contact surfaces which are arranged in such a manner that, by rotation of the sliding element, the ejection element can be released from a fixing position. The locking element preferably has an extension and the sliding element a corresponding guide surface.

The base element and the sliding element advantageously have corresponding guide elements which are designed and arranged in such a manner that the sliding element is rotatable relative to the base element only in the proximal end region.

By this, it is avoided that the user, before the proximal end region, already carries out a rotation of the sliding element relative to the base element, which could lead to a malfunction, in particular to a premature or non-materializing triggering of the ejection spring.

For this purpose, a guide slot or a guide groove is advantageously formed on one of the two elements, base element and sliding element, and runs rectilinearly in the injection direction, but, in the proximal end region, reproduces the rotation of the sliding element relative to the base element, in particular preferably the guide slot or guide groove are thus formed in an L shape. A guide extension is preferably formed on the other of the two elements, in particular a pin which engages in the aforementioned guide groove or the guide slot.

The sliding element preferably has guide slots for the extension of the cannula upper part, said guide slots being arranged in such a manner that, after rotation of the sliding element into the proximal end region, the cannula upper part is displaceable counter to the injection direction. By this, an ejection operation is possible in a structurally simple manner without the sliding element having to be moved counter to the injection direction.

In the advantageous refinement with provision of an ejection element, in particular of an ejection spring, during the ejection operation, displacement of the cannula upper part with cannula counter to the injection direction therefore preferably takes place relative to the base element and relative to the sliding element, and therefore, during the ejection operation, no or at least a slight further displacement takes place between base element and sliding element.

The aforementioned bevel is preferably formed on the sliding element at a proximal end of the aforementioned guide slots. This results in a structurally simple construction.

The injector advantageously has a counterforce spring which is arranged between base element and sliding element in a manner acting counter to a displacement of the sliding element in the injection direction. This ensures that the injection operation is started only by pressure on the sliding element and, for example, does not already take place solely on the basis of the force of the weight of the sliding element.

BRIEF DESCRIPTION OF THE DRAWINGS

Further preferred features and embodiments will be explained below with reference to an exemplary embodiment and the Figures, in which.

DETAILED DESCRIPTION

The same reference signs in the Figures denote identical or identically acting elements.

Figure 1:
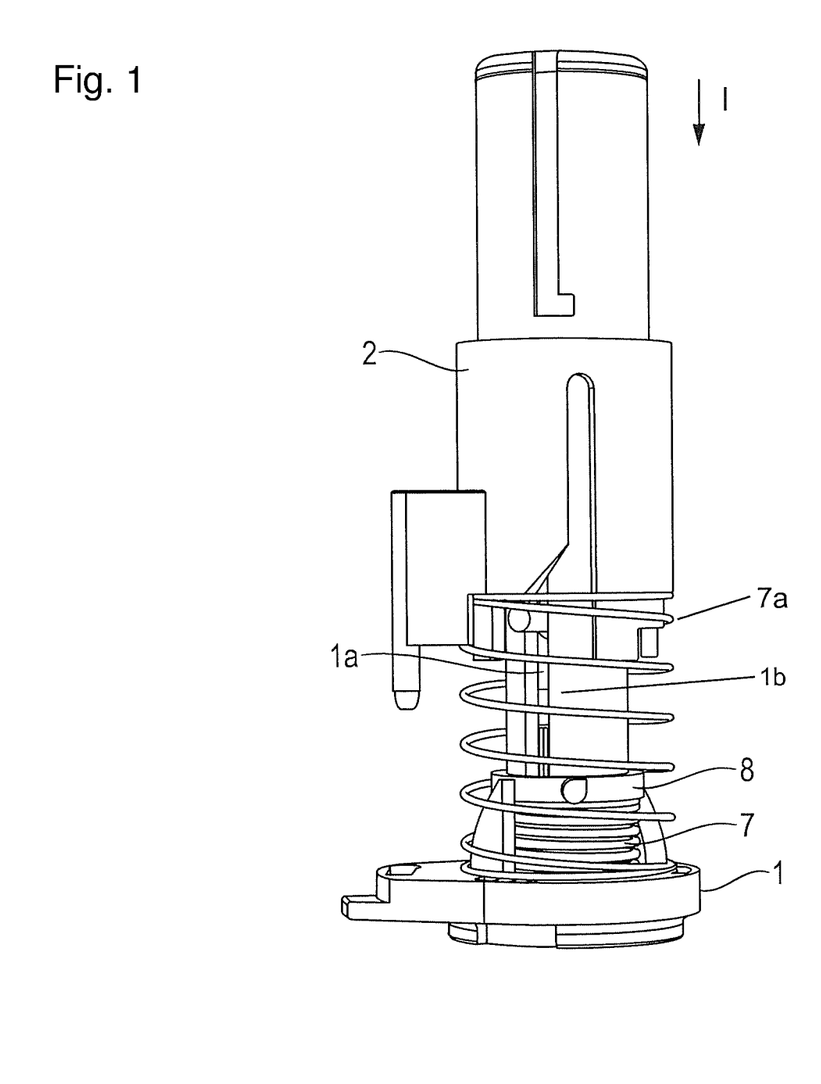
FIG. 1 shows a side view of an exemplary embodiment of an injector according to the invention for transcutaneously introducing a sensor into a patient.

FIG. 1 shows the exemplary embodiment of the injector according to the invention in a side view. The injector has a base element 1 and a sliding element 2. The sliding element is arranged on the base element so as to be displaceable in an injection direction I.

The injector can additionally have a housing which is arranged on the base element and surrounds the base element and the lower part, in particular the lower half of the sliding element 2 according to FIG. 1. For reasons of better representability, the housing is not shown in the Figures.

In order to use the injector, a base plate is stuck onto the patient's skin and the injector is attached to the base plate by a bayonet closure formed on the lower side of the base element, and therefore the injector is arranged releasably on the base plate and therefore releasably on the patient. Similarly, the injector can already be attached to the base plate in the delivery state, and therefore injector and base plate are stuck onto the patient's skin.

In all of the Figures, the patient's tissue is therefore located on the lower side, and therefore, in the Figures, the lower regions show proximal regions and the upper regions show distal regions.

The base element has a region which is designed approximately as a hollow cylinder and which approximately surrounds a cannula 3 with a cannula upper part 4 and a holding element 5. These elements are illustrated separately in FIGS. 2A, 2B, 3, 4a and 4B:

The cannula 3 is embedded at its distal end in a central element 4a (see FIG. 4B) of the cannula upper part 4 and connected fixedly thereto. The holding element 5 is arranged below the cannula upper part 4, said holding element 5 having, in the distal region, an indentation in which the cannula upper part 4 engages, wherein the holding element 5 is arranged on the cannula upper part 4 with a slight press fit.

The cannula upper part 4 furthermore has two extensions 4b, 4c which are arranged on opposite sides and extend perpendicularly to the longitudinal extent of the cannula 3 and therefore perpendicularly to the injection direction I.

Figure 2A:
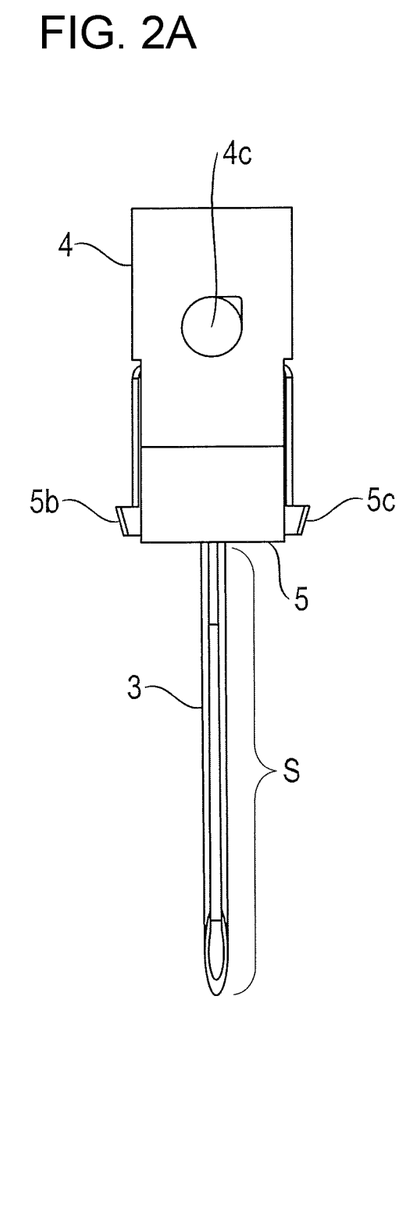
FIGS. 2A and 2B show side views of cannula, cannula upper part and holding element of the injector.
Figure 2B:
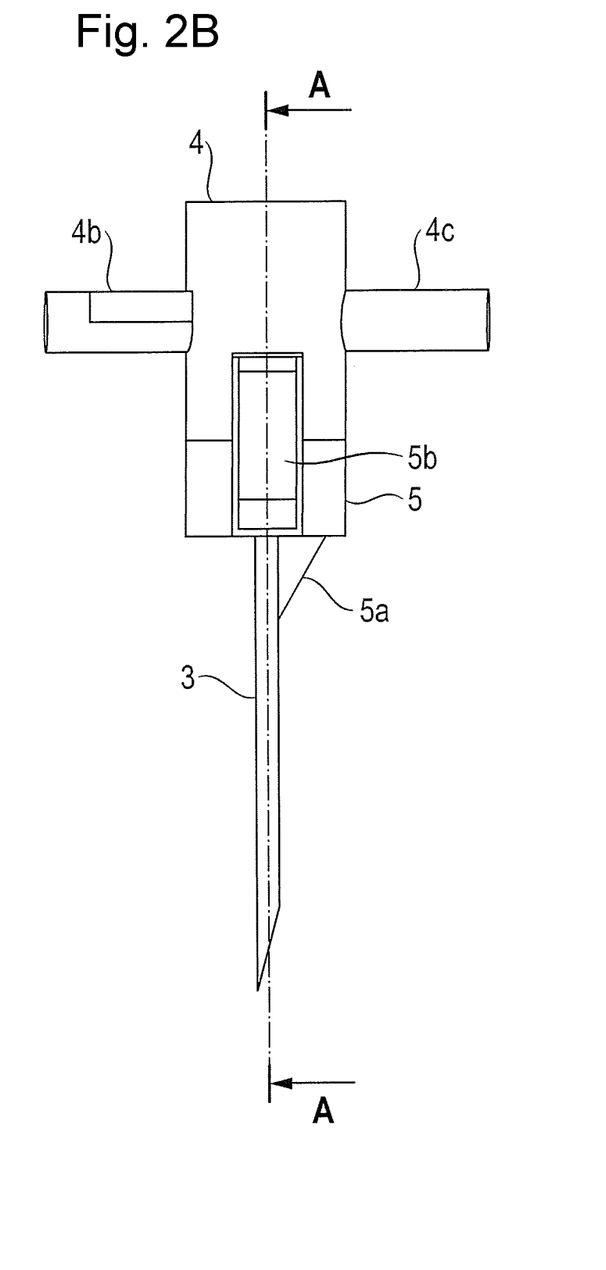

FIG. 2A shows here a side view with a top view of the end side of the extension 4c, and FIG. 2B shows a side view with a longitudinal extent of the extensions 4b and 4c, the longitudinal extent lying in the plane of the drawing.

Figure 3:
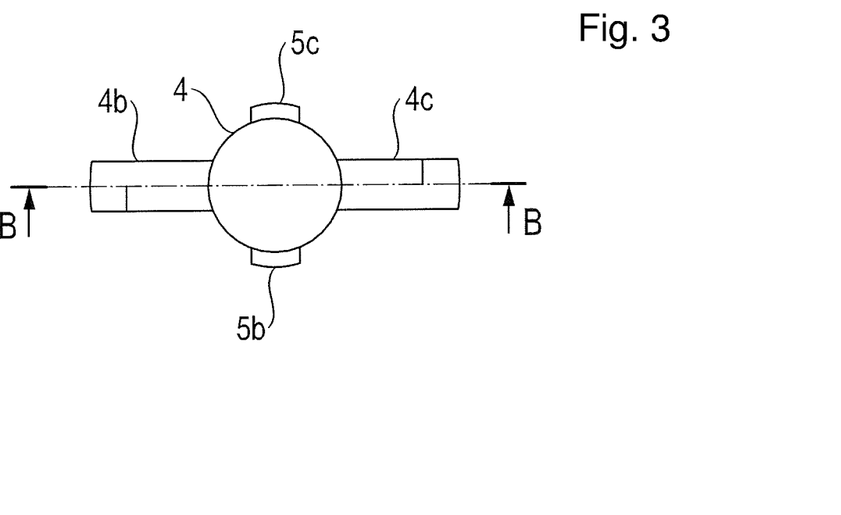
FIG. 3 shows a top view from above of the elements according to FIG. 2.
Figure 4A:
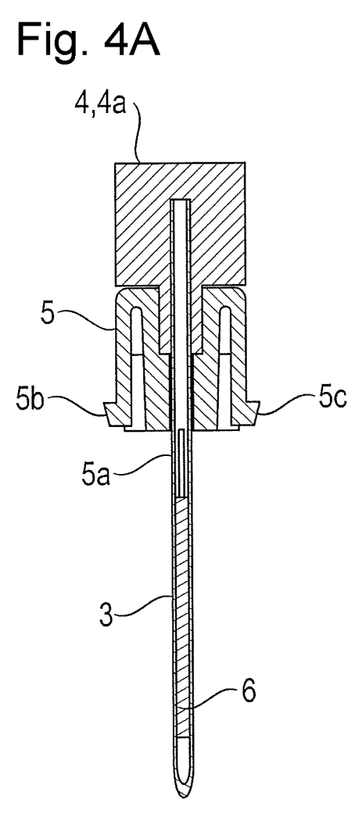
FIGS. 4A and 4B show sectional illustrations of the elements from FIGS. 2A and 2B.
Figure 4B:
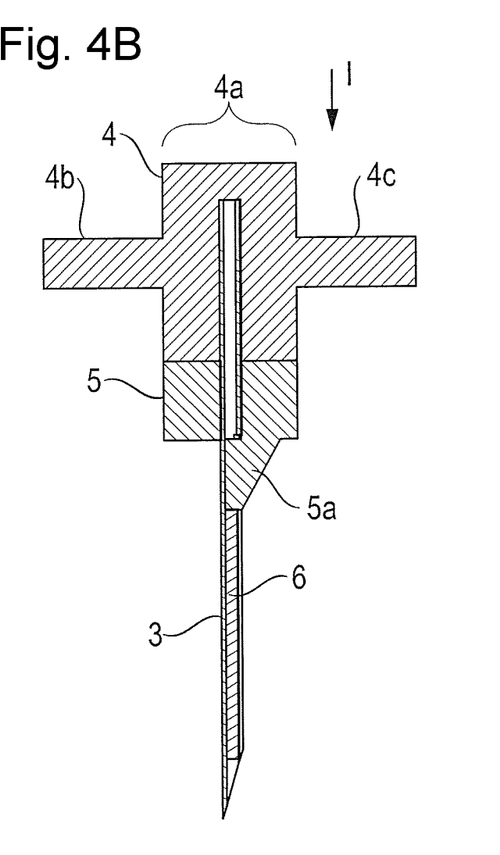

FIG. 3 shows a top view from above of the cannula upper part 4. FIG. 4A shows a section according to the intercepting line A-A in FIG. 2B, wherein the sectional plane lies perpendicularly to the plane of the drawing of FIG. 2A. FIG. 4B shows a section according to the intercepting line B-B in FIG. 3, wherein the sectional plane likewise lies perpendicularly to the plane of the drawing according to FIG. 3.

As is apparent, for example, in FIG. 2A, the cannula 3 has a slot in a proximal region S. FIG. 2A shows the top view from the front of the slot of the cannula 3. A sensor 6 is arranged in the cannula 3, as is apparent, for example, in FIGS. 4A and 4B.

This sensor is intended to be inserted transcutaneously into the patient's tissue by the injector in order optically to determine readings by a detection element/detection unit designed as a detector. The basic principles of such an optical measurement are described in WO2016128334A1 and WO2006092317A1.

The insertion of other sensors, in particular sensors with electrodes for electrically sensing readings is likewise possible in a same manner.

As is apparent in particular in FIGS. 2B, 4A and 4B, the holding element 5 has a cam 5a which, in the region of the distal end of the sensor 6, engages in the cannula 3 through the slot therein and therefore lies against the upper distal end of the sensor 6 (see FIG. 4B).

The holding element 5 furthermore has fixing arrangement 5b and 5c in the form of latching lugs, and therefore, at the end of an injection operation, the holding element 5 can be automatically locked on the base element.

Figure 5:
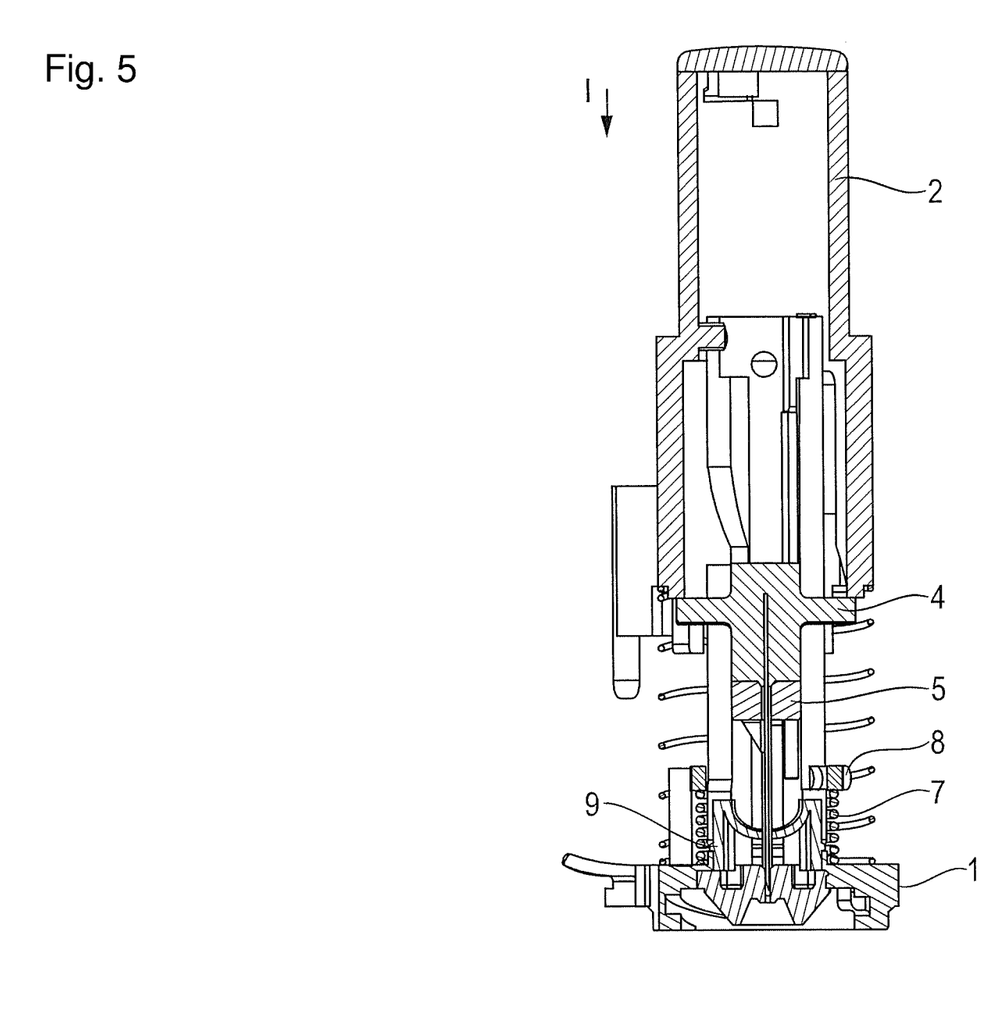
FIG. 5 shows a sectional illustration of the injector before the injection operation.

FIG. 5 shows a sectional illustration of the injector, wherein the sectional plane runs through the central axis of the cannula 3 and therefore through the injection axis. The state is illustrated prior to the injection operation, the state constituting the delivery state: cannula and sensor are located within the injector, in particular within the base element 1.

Cannula 3 with sensor 6, holding element 5 and central element 4a of the cannula upper part 4 are arranged within a region of approximately cylindrical design of the base element 1. Said cylindrical region has guide slots which run rectilinearly in the injection direction I and of which a guide slot 1a is visible in FIG. 1.

The extensions 4b and 4c of the cannula upper part 4 penetrate the approximately cylindrical region of the base element 1. As is apparent in FIG. 5, the sliding element 2 acts on the extensions 4b and 4c outside the cylindrical region of the base element 1. The sliding element 2 is therefore guided displaceably in the injection direction on an outer wall of the cylindrical region of the base element 1, and central element 4a of the cannula upper part 4 and holding element 5 are guided displaceably in the injection direction on the inner side of the cylindrical region of the base element 1. The cylindrical region of the base element 1 therefore forms a guide wall 1b for said elements.

If the user now presses the sliding element 2 downwards in the injection direction, the force is transmitted via the extensions 4b and 4c to the central element 4a and therefore to the cannula 3. The force is also transmitted via the central element 4a to the holding element 5, and therefore said elements and also the sensor 6 are moved in the injection direction.

Figure 6:
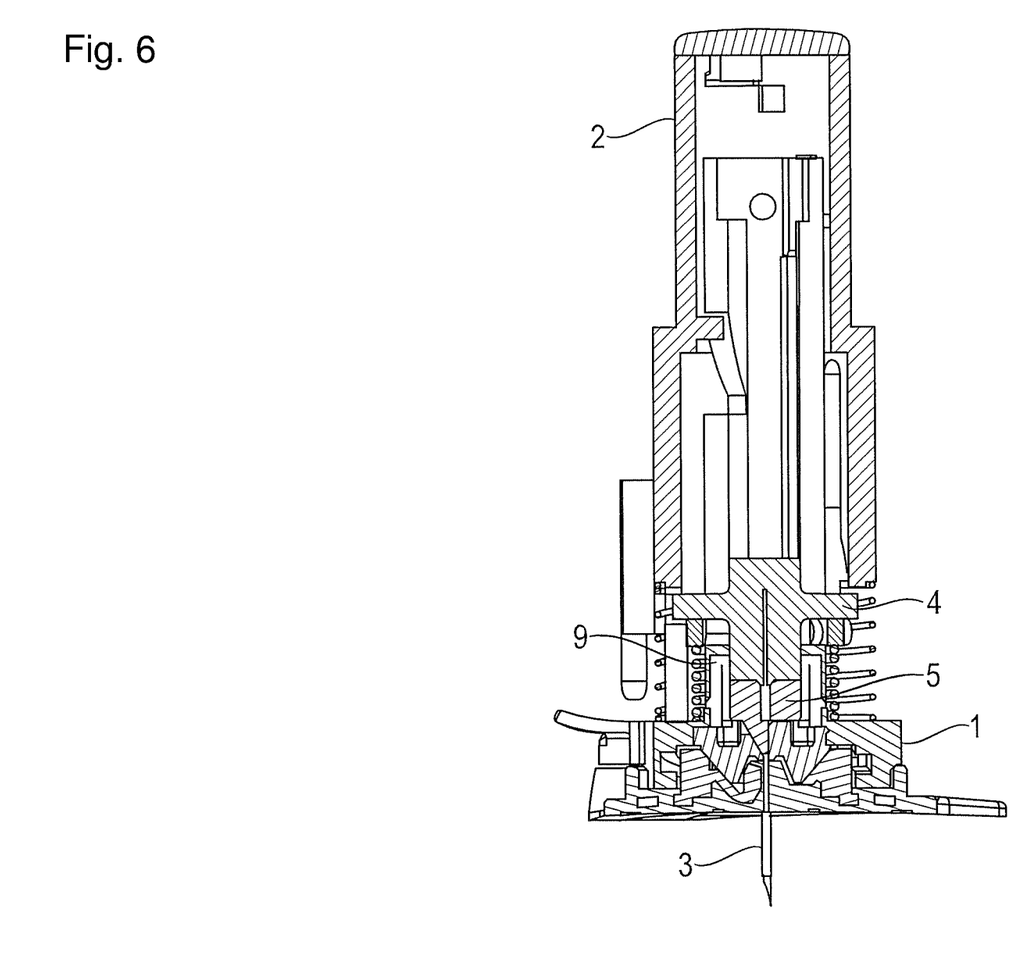
FIG. 6 shows a sectional illustration of the injector after the injection operation has ended.
Figure 7:
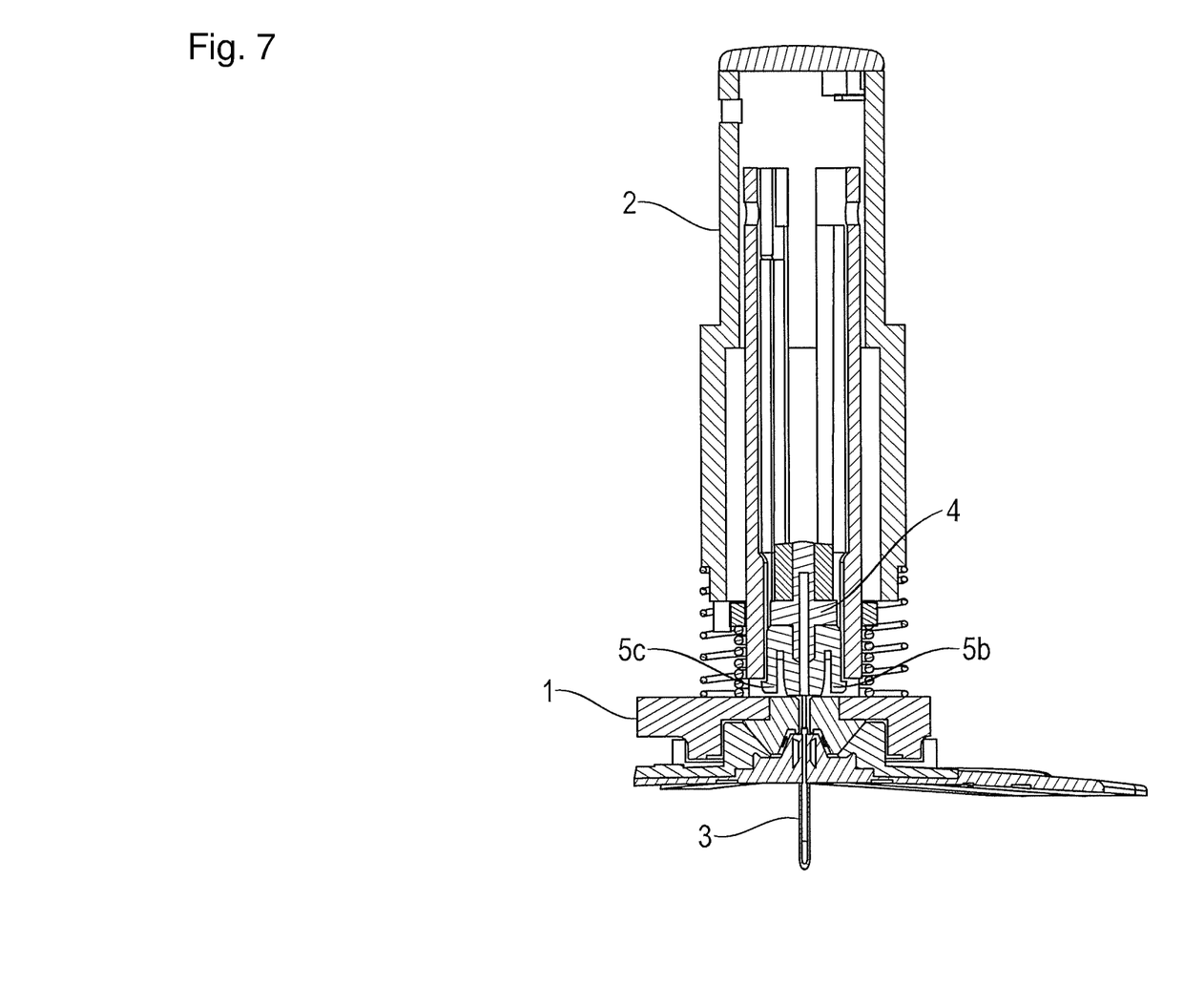
FIG. 7 shows a further sectional illustration at the end of the injection operation, wherein the sectional plane lies perpendicular to the sectional plane according to FIG. 6.

FIG. 6 shows the end of the injection operation: the sliding element 2 is completely pressed down, the cannula 3 with the sensor 6 has penetrated transcutaneously into the patient's tissue and the fixing arrangement 5b and 5c in the form of latching lugs have latched into corresponding recesses of the base element 1, as is apparent in FIG. 7.

At the end of the injection operation, the holding element 5 is therefore automatically fixed to the base element 1.

During the subsequent ejection operation, the cannula upper part 4 is moved upward counter to the injection direction I, and therefore the cannula 3 is pulled out of the patient's tissue. Since, however, the holding element 5 is fixed to the base element 1, the holding element does not undertake said movement counter to the injection direction. A press fit which is possibly present between holding element 5 and cannula upper part 4 is overcome by the fixing by the latching lugs. Since the cam 5a of the holding element 5 continues to engage in the slot of the cannula 3 at the distal end of the sensor in the cannula, it is thereby prevented that, when the cannula 3 is pulled out, the sensor is also pulled out of the patient's tissue. In particular, an adhesion or rubbing between sensor and cannula can thereby also be overcome.

After the ejection operation is finished, the injector is removed from the previously mentioned base plate, and therefore only base plate and sensor 6 remain on the patient. The holding element 5 and the sensor 5 are therefore designed as separate units.

The injector according to the present exemplary embodiment furthermore has an ejection element in the form of an ejection spring 7 and a locking element in the form of an ejection spring holding element 8 for the ejection element. As is apparent in FIG. 1, in the delivery state, the ejection spring 7 is arranged compressed between base element 1 and ejection spring holding element 8. The ejection spring 7 surrounds the cylindrical region of the base element 1 in a proximal region.

The ejection spring holding element 8 is of substantially annular design and has a pin both on the inner side and on the outer side. By the inner pin, the ejection spring holding element is fixed releasably to a guide of the base element running perpendicularly to the injection direction, see FIG. 8A. In the region marked by a circle in FIG. 8A, the inner pin of the ejection spring holding element 8 engages in a guide on the outer wall of the base element 1, and therefore no expansion of the ejection spring 7 is possible in this state. As explained in more detail below, sliding element 2 and ejection spring holding element 8 are designed so as to interact in such a manner that, at the end of the injection operation, rotation of the ejection spring holding element 8 takes place, and therefore the pin of the ejection spring holding element 8 is rotated to the left in the illustration according to FIG. 8A and thus enters the region of the guide slot 1a of the base element 1, and therefore expansion of the ejection spring 7 is possible.

Figure 8A:
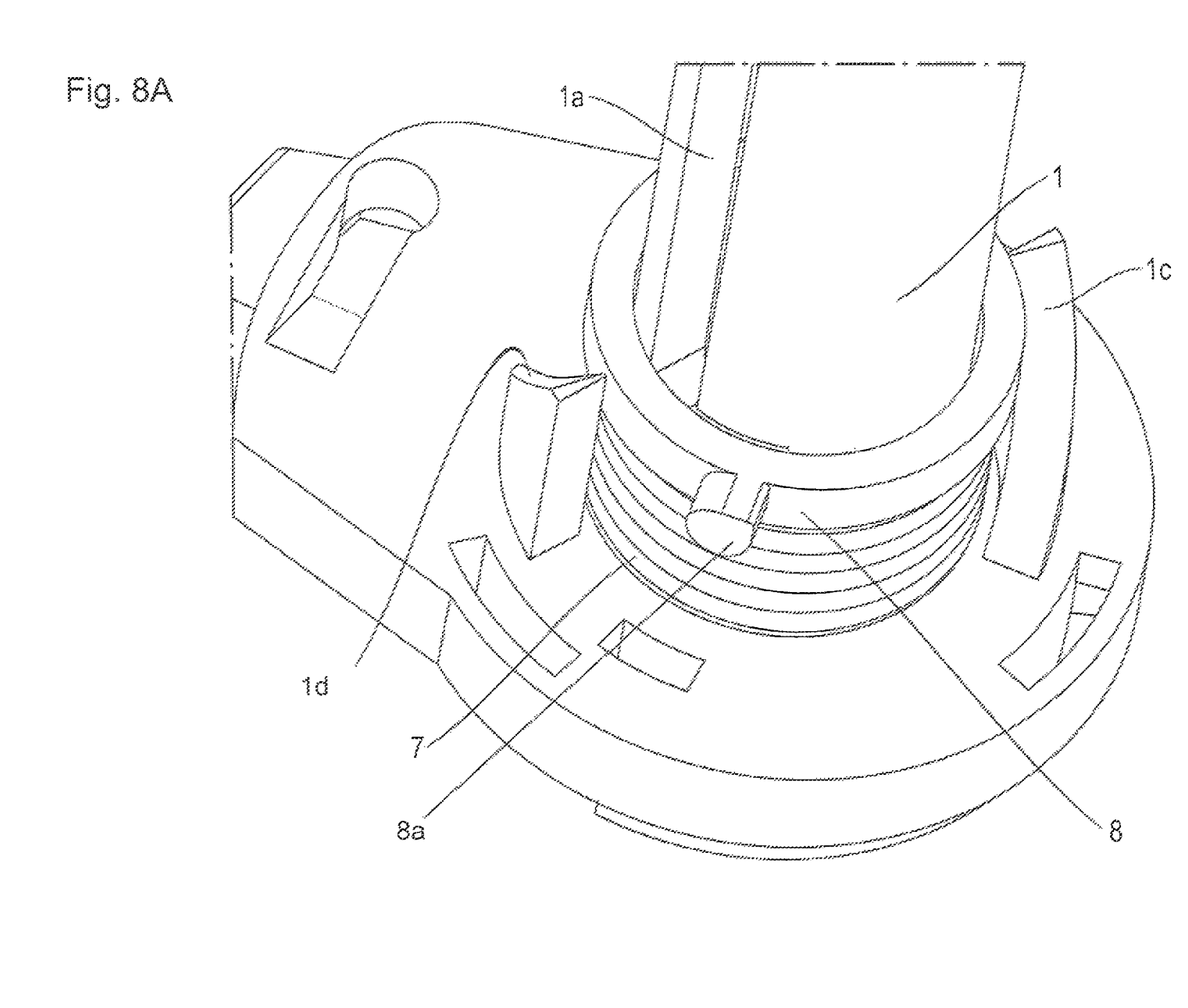
FIGS. 8A and 8B show detailed views of the detector with an ejection spring holding element.
Figure 8B:
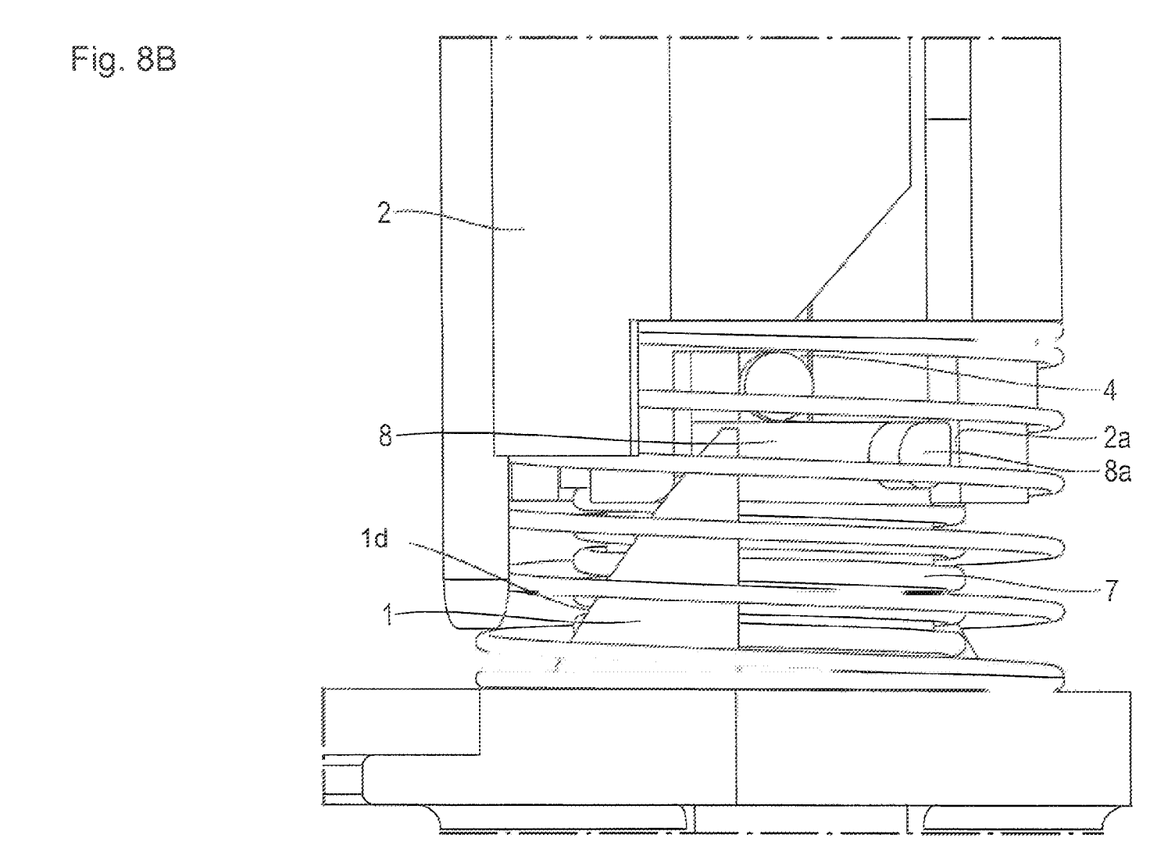

As is apparent in FIGS. 8A and 8B, the base element has, in a proximal region, two guides 1c and 1d which are designed as bevels, i.e. oblique surfaces, and enter into contact with corresponding contact surfaces of the sliding element 2 at the end of the injection operation. If the sliding element is pressed down further in said end region, rotation of the sliding element relative to the base element about the injection axis takes place because of the bevels 1c and 1d. For better clarification, elements, such as, for example, the sliding element, are not illustrated in FIG. 8A.

As is apparent in FIG. 8B, the ejection spring holding element 8 has an outer extension 8a which is in the form of a pin and, upon rotation of the sliding element 2, comes into contact with a corresponding guide surface 2a of the sliding element 2 such that rotation of the ejection spring holding element 8 takes place as described previously.

Figure 9:
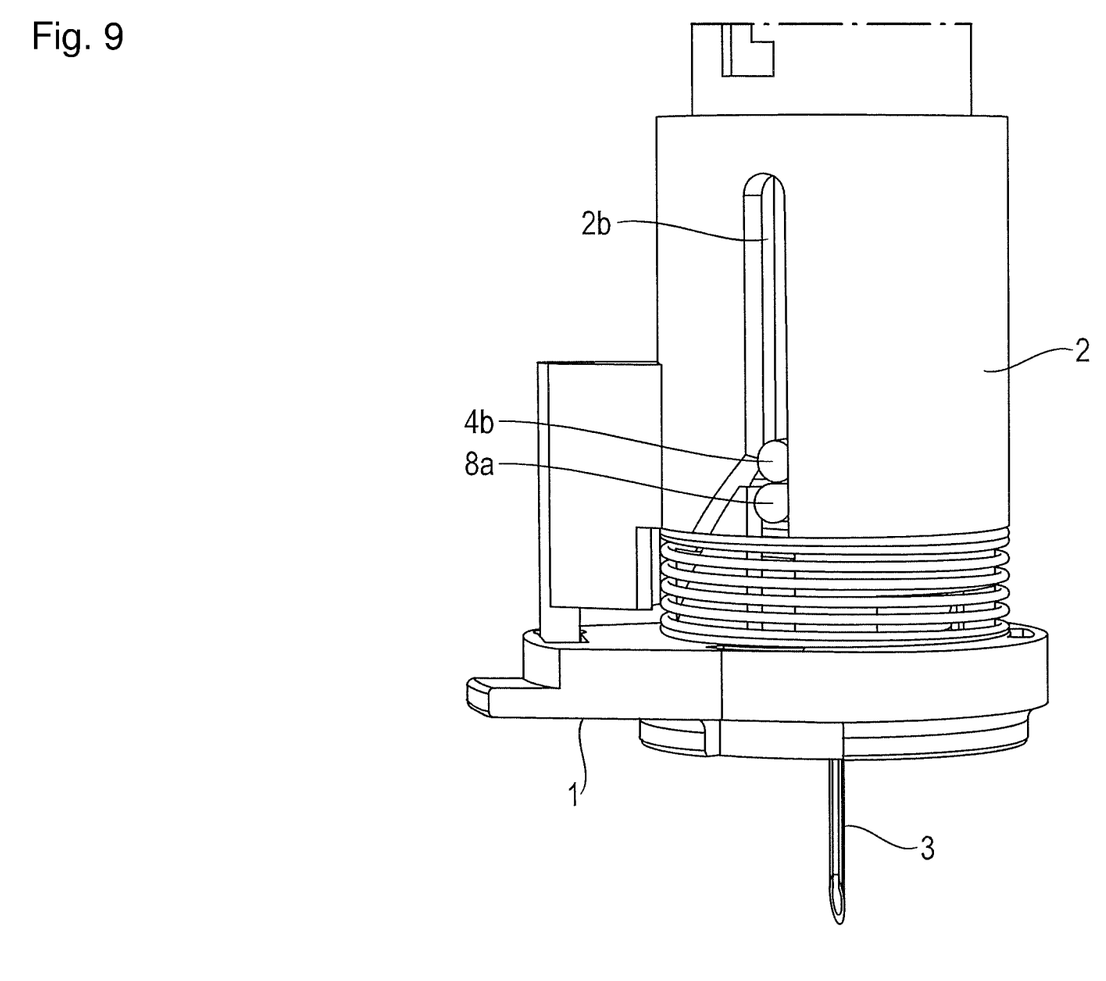
FIG. 9 shows a detailed view of the injector in the proximal end region of the injection operation.

FIG. 9 shows the state with the sliding element 2 completely pressed downward, and therefore the rotation of the sliding element 2 relative to the base element 1 is also finished. As is apparent, in said end state of the injection operation, both the outer pin 8a of the ejection spring holding element 8 and the extension 4b of the cannula upper part 4 are located in the region of a guide slot 2B of the sliding element 2. On the opposite side (not apparent), the extension 4c of the cannula upper part 4 is correspondingly located in a radially oppositely arranged guide slot of the sliding element 2.

In this state, there is therefore no limit for the extensions 4b and 4c and for the outer pin 8a in respect of a movement counter to the injection direction. As a result, an expansion of the ejection spring 7 takes place, and therefore ejection spring holding element 8 and cannula upper part 4 are pressed upward in an ejection operation counter to the injection direction. The holding element 5, by contrast, does not change the position because of the latched holding elements.

The cannula 3 is therefore pulled out of the patient's tissue, with the sensor 6 being prevented by the cam 5a of the holding element 5 from being pulled out.

Figure 11:
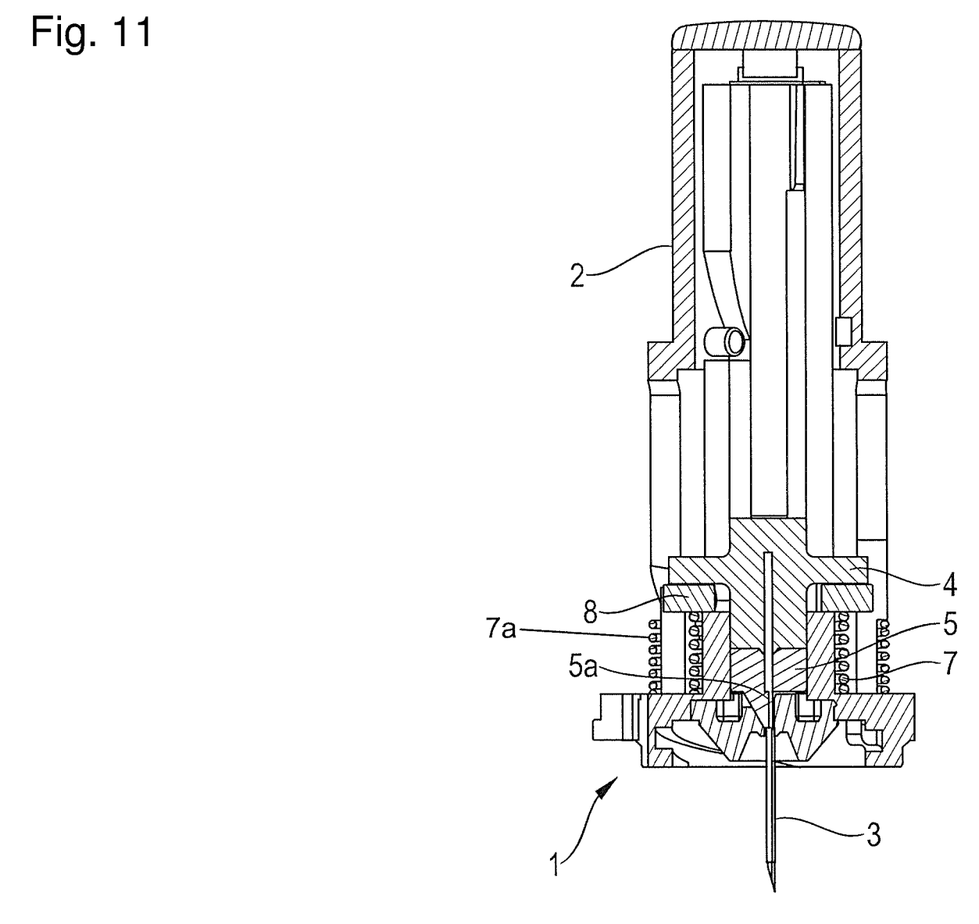
FIG. 11 shows a sectional illustration of the view according to FIG. 9.

FIG. 11 illustrates the configuration from FIG. 9 as a sectional image, wherein the injection axis lies within the sectional plane and the section runs along the intercepting line B according to FIG. 3. In particular the compressed ejection spring 7 is apparent here, said ejection spring acting firstly on the holding element 8 and secondly on the base element 1. A counterforce spring 7a is arranged concentrically with respect to the ejection spring 7, but with a greater radius, said counterforce spring firstly reacting on the base element 1 and secondly on the sliding element 2. This counterforce spring is also completely compressed in this configuration. The counterforce spring serves in particular for the purpose of avoiding dropping down of the sliding element 2 because of gravitational force and for providing the user with an approximately constant counterforce during the injection operation in order to permit a uniform injection, in particular a uniform speed of penetration of the cannula 3 into the patient.

Figure 10:
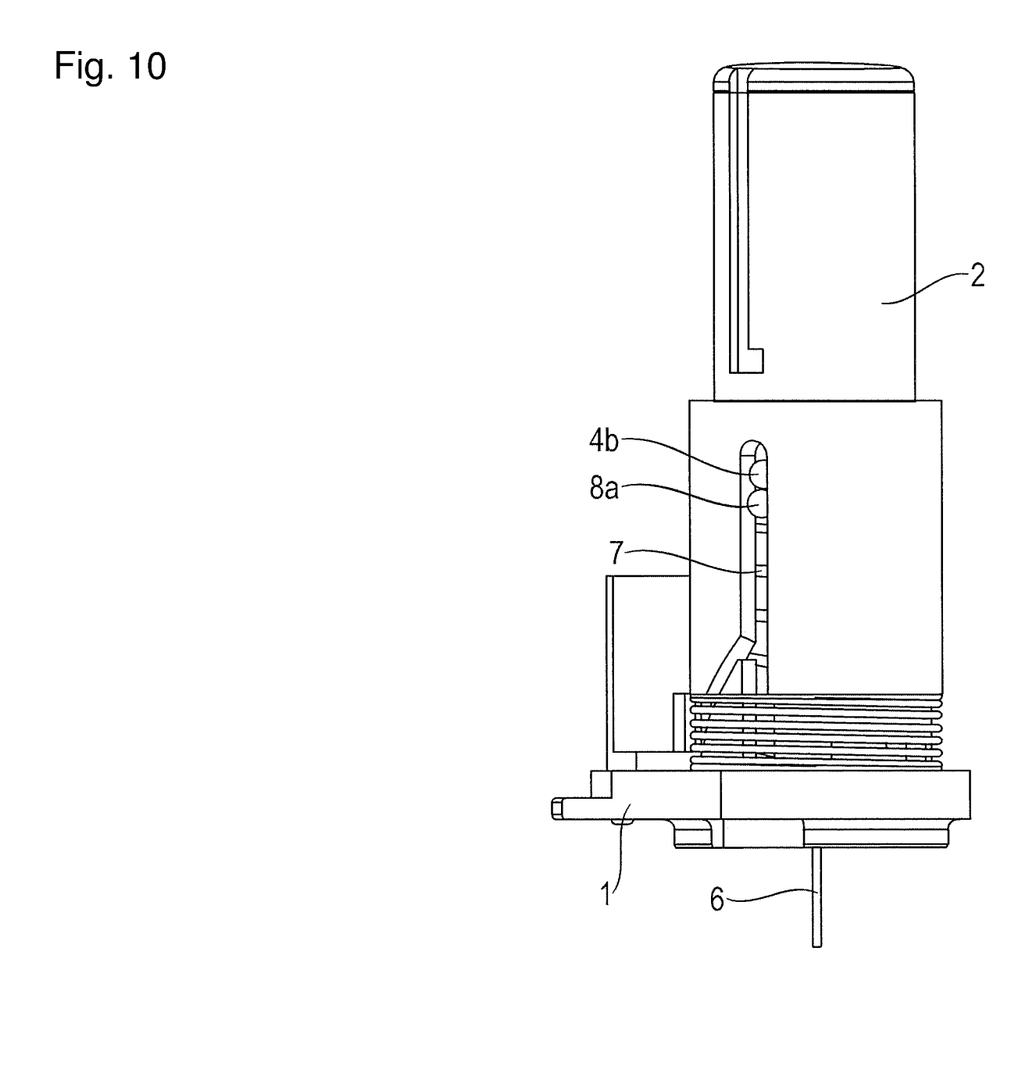
FIG. 10 shows a side view of the injector after the ejection operation is finished.

FIG. 10 illustrates the view according to FIG. 9, but after the ejection operation has finished:

As previously described, at the end of the injection operation the holding element 8 is rotated about the injection axis, and therefore it is transferred from a fixing position in which no movement of the holding element in the ejection direction, i.e. counter to the injection direction I, is possible, into an ejection position in which a movement can take place in the ejection direction.

As already described with respect to FIG. 8A, the holding element 8 has, on the inner side, a pin which, according to the fixing position illustrated in FIG. 8A, is arranged in a horizontally running slot of the base element 1, and therefore no movement in the ejection direction (upward in FIG. 8A) is possible.

At the end of the injection operation, the holding element 8 is rotated about the injection axis, in the clockwise direction according to FIG. 8A, and therefore the inner pin of the holding element 8 comes to lie in alignment with the guide slot 1*a* of the base element 1. By this, a movement of the guide element 8 in the ejection direction (upward) is therefore possible. This rotation of the holding element 8 takes place since, at the end of the injection operation, because of the bevels 1*d* and 1*c* of the base element 1 and the corresponding bevels of the sliding element 2, rotation of the sliding element about the injection axis (in the present case in the clockwise direction) takes place and, by the surface 2*a* of the sliding element 2 that acts on the outer pin of the holding element 8, the rotation is transmitted to the holding element 8.

If the holding element 8 is in an ejection position, expansion of the expansion spring 7 is possible: by this, the holding element 8 is pressed upward and this movement is transmitted to the cannula upper part 4 and therefore also to the cannula 3, and therefore the cannula 3 is pulled out of the patient in an ejection operation. Due to the previously described holding element 5, the sensor 6, however, remains transcutaneously in the patient.

FIG. 10 now shows the situation after the ejection operation is finished: the ejection spring 7 is in an expanded state, holding element 8 and cannula upper part 4 (and also cannula 3) are pushed upward and located within the base element 1. However, the position of the sliding element 2 is unchanged, and therefore, as before, the outer counterforce spring is in a compressed state.

Figure 12:
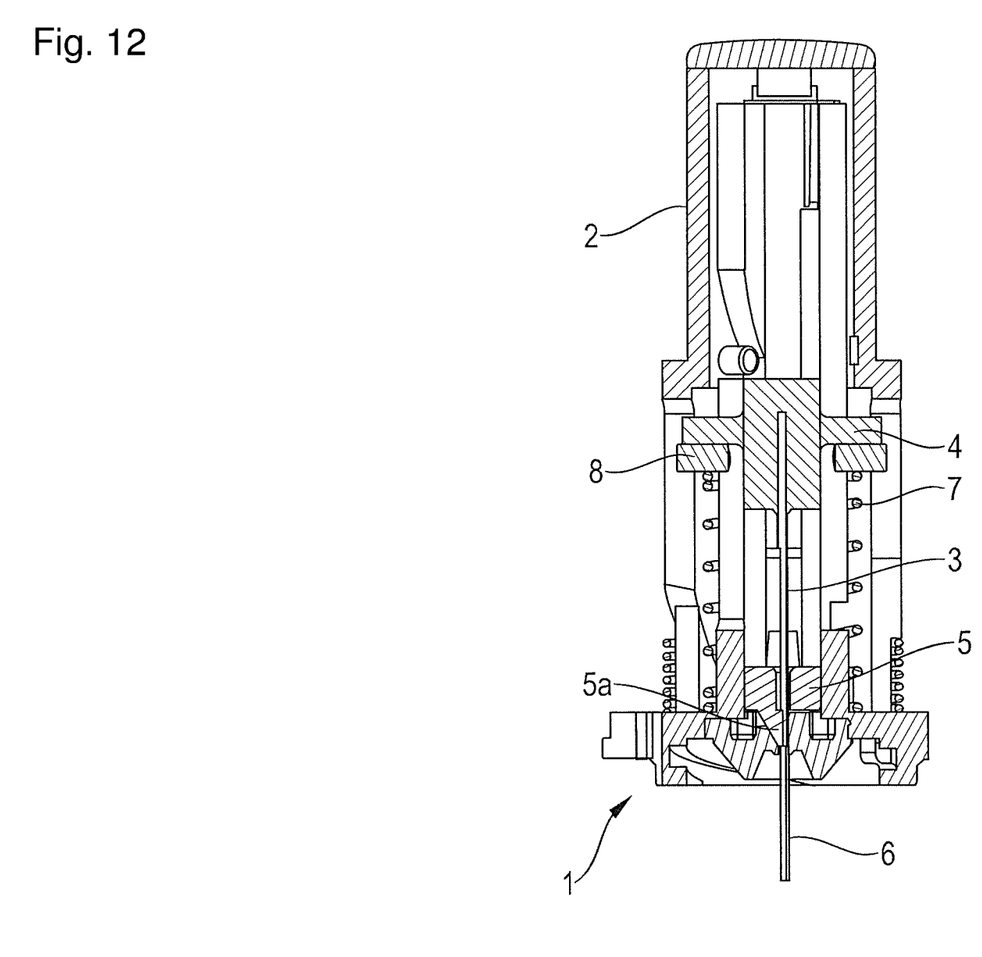
FIG. 12 shows a sectional illustration of the view according to FIG. 10.

FIG. 12 illustrates a section analogously to FIG. 11, but at the end of the ejection operation according to FIG. 10.

The injector according to the present exemplary embodiment furthermore has a cannula guide 9 for the cannula 3, as is apparent in particular in FIGS. 5 and 6:

The cannula guide 9 serves to guide the cannula in particular during the injection operation, but also during the ejection operation, in order to avoid tilting or lateral slippage. For this purpose, the cannula guide 9 is arranged on two opposite sides on the base element 1 and centrally has an elastic guide surface with an opening which is penetrated by the cannula 3 and divides the cannula guide 9 into two halves. FIG. 5 illustrates the state before the beginning of the injection. The cannula 3 is guided here in a proximal region by the cannula guide 9, and therefore, during the subsequent injection, tilting or lateral displacement is avoided.

After the injection operation is finished, the holding element 5 and the cannula upper part 4 reach the region of the cannula guide 9. On account of the division of the cannula guide 9 into two, the elastic elements of the cannula guide 9 can be pushed to the right and left by the holding element 5. This is the case in FIG. 6.

The invention claimed is:

1. An injector for transcutaneously introducing a sensor into a patient, the injector comprising:
   a cannula,
   a sensor arranged in the cannula,
   a base element,
   a sliding element arranged displaceably on the base element in an injection direction,
   a slot at least in a proximal region of the cannula, the slot extending in a longitudinal direction of the cannula, and
   a holding element on the base element and engaged in the cannula through the slot and against a distal end of the sensor, wherein
   at least one of the holding element or the base element have at least one fixing arrangement, wherein the fixing arrangement is configured to automatically lock the holding element on the base element,
   the sliding element is adapted for transcutaneously introducing the cannula having the sensor into the patient in an injection operation,
   the holding element is arranged displaceably on the base element such that when pulling the cannula out of the patient in an ejection operation, the holding element prevents the sensor from being pulled out, and
   the holding element and the sensor are separable units and configured such that when the cannula, the base element, the sliding element, and the holding element are removed from the patient in a removal operation, the sensor remains in the patient.

2. The injector according to claim 1, wherein the fixing arrangement comprises a latching element, and one of the holding element or the base element includes the latching element and the other of the holding element or the base element has corresponding depressions configured to engage the latching element.

3. The injector according to claim 1, wherein the cannula is arranged with a distal end thereof on a cannula upper part, which is arranged displaceably on the base element, and the sliding element and the cannula upper part are adapted to interact such that, during the injection operation, the cannula upper part is displaceable in an injection direction by the sliding element.

4. The injector according to claim 3, wherein during the injection operation the holding element is configured to be displaced in the injection direction by the cannula upper part.

5. The injector according to claim 4, wherein the cannula upper part has a central element on which the cannula is arranged and has at least one guide extension, and the base element has at least one guide wall with a guide slot, the guide slot engaging the guide extension of the cannula upper part, and configured for guiding the cannula upper part in the injection direction, and the sliding element is configured to engage on the guide extension on a side of the guide wall which faces away from the central element of the cannula upper part.

6. The injector according to claim 1, further comprising an ejection spring and an ejection spring holding element, the ejection spring holding element is on the base element, and the ejection spring is fixed in a compressed or expanded state by the ejection spring holding element.

7. The injector according to claim 6, wherein the sliding element is configured to release the ejection spring holding element at the end of the injection operation from a fixing position.

8. The injector according to claim 7, wherein the ejection spring holding element is releasable by the sliding element from the fixing position by rotation of the ejection spring holding element about an injection axis.

9. The injector according to claim 7, wherein the sliding element and the ejection spring holding element are arranged on the base element so as to be rotatable about a common injection axis.

10. The injector according to claim 9, wherein at least one of the base element or the sliding element have at least one bevel which is arranged such that, during the injection operation, the sliding element is adapted to rotate relative to the base element at a proximal end region when the sliding element is displaced in the injection direction.

11. The injector according to claim 10, wherein the sliding element and the ejection spring holding element have corresponding contact surfaces which are arranged such that the ejection element is releasable from the fixing position by rotation of the sliding element.

12. The injector according to claim 11, wherein the ejection spring holding element has an extension and the sliding element has a corresponding guide surface.

13. The injector according to claim 12, wherein the base element and the sliding element have corresponding guide elements that allow rotation of the sliding element relative to the base element only in the proximal end region.

14. The injector according to claim 13, wherein the sliding element has guide slots for the cannula upper part, said guide slots being arranged such that, after rotation of the sliding element in the proximal end region, the cannula upper part is displaceable counter to the injection direction.

15. The injector according to claim 14, wherein the at least one bevel is formed on the sliding element at a proximal end of the guide slots.

16. The injector according to claim 15, further comprising a counterforce spring arranged between the base element and the sliding element that acts counter to a displacement of the sliding element in the injection direction.

* * * * *